(12) United States Patent
Schoenbach et al.

(10) Patent No.: US 10,143,519 B2
(45) Date of Patent: Dec. 4, 2018

(54) METHOD AND SYSTEM FOR TREATING A BIOLOGICAL TARGET REGION USING PULSED ELECTROMAGNETIC RADIATION

(75) Inventors: Karl H. Schoenbach, Norfolk, VA (US); Shu Xiao, Norfolk, VA (US)

(73) Assignee: OLD DOMINION UNIVERSITY RESEARCH FOUNDATION, Norfolk, VA (US)

( * ) Notice: Subject to any disclaimer, the term of this patent is extended or adjusted under 35 U.S.C. 154(b) by 1716 days.

(21) Appl. No.: 13/378,532

(22) PCT Filed: Apr. 29, 2010

(86) PCT No.: PCT/US2010/032979
§ 371 (c)(1),
(2), (4) Date: Dec. 15, 2011

(87) PCT Pub. No.: WO2010/151370
PCT Pub. Date: Dec. 29, 2010

(65) Prior Publication Data
US 2012/0089209 A1    Apr. 12, 2012

Related U.S. Application Data

(60) Provisional application No. 61/220,148, filed on Jun. 24, 2009.

(51) Int. Cl.
*A61B 18/12* (2006.01)
*A61B 18/18* (2006.01)
(52) U.S. Cl.
CPC .............................. *A61B 18/1815* (2013.01)

(58) Field of Classification Search
CPC ........... A61B 18/18; A61N 7/02; A61N 7/025
See application file for complete search history.

(56) References Cited

U.S. PATENT DOCUMENTS

| 2006/0142748 | A1* | 6/2006 | Foreman et al. ............... 606/27 |
| 2007/0100390 | A1* | 5/2007 | Danaek .................. A61N 1/403 607/42 |
| 2007/0239143 | A1* | 10/2007 | Altshuler et al. ................. 606/9 |
| 2008/0228063 | A1* | 9/2008 | Turner et al. ................. 600/411 |

(Continued)

FOREIGN PATENT DOCUMENTS

WO    2009046275 A1    4/2009

OTHER PUBLICATIONS

International Search Report and Written Opinion dated Jul. 2, 2010 under International Patent Application No. PCT/US2010/032979 (7 pages).

*Primary Examiner* — Linda Dvorak
*Assistant Examiner* — Yasamin Ekrami
(74) *Attorney, Agent, or Firm* — Nixon Peabody LLP; Eduardo J. Quiñones

(57) ABSTRACT

A method of treating a patient is described herein. The method can include the steps of identifying a target that contains biological tissue and directing one or more pulses of electromagnetic radiation at the target. The pulses of electromagnetic radiation can cause a temperature increase per unit of time in the biological tissue. Additionally, the temperature increase per unit of time can cause the change in the cell function in the biological tissue and can be within a range of approximately one degree Celsius per second to approximately one degree Celsius per microsecond.

14 Claims, 5 Drawing Sheets

(56) References Cited

U.S. PATENT DOCUMENTS

2009/0125091 A1\* 5/2009 Schoenbach et al. ........ 607/156
2010/0010486 A1\* 1/2010 Mehta .................... A61B 18/14
606/41

\* cited by examiner

METHOD AND SYSTEM FOR TREATING A BIOLOGICAL TARGET REGION USING PULSED ELECTROMAGNETIC RADIATION

CROSS-REFERENCE TO RELATED APPLICATIONS

This application is a § 371 National Stage Entry of International Patent Application No. PCT/US2010/032979 filed Apr. 29, 2010, which is a Non-Provisional Application of U.S. Provisional Application No. 61/220,148 filed Jun. 24, 2009, the entire contents of which are incorporated herein by reference.

FIELD OF THE INVENTION

The subject matter herein generally relates to treating patients with electromagnetic radiation and more particularly, treating patients with electromagnetic radiation to cause rapid heating of tissue and to thereby induce cell death.

BACKGROUND

Heating of tissues can be used as a form of cancer treatment. Such heating, known as hyperthermia therapy, is generally used as a method to treat cancer, either by just its thermal effects or in combination with other agents, e.g. radiation or pharmaceutical cancer treatments. That is, this heating process is used to kill cancer cells and/or damage cancer cells, making such cells more sensitive to collateral modes of treatment. In general, such therapies require precise control of temperature, as increasing the temperature of tissue to 50 Celsius ("C") can cause coagulation necrosis (i.e., ablation). Typically, such therapies are carried using different forms of energy, including microwaves, radio waves and ultrasound.

In general, the irradiation time for hyperthermia depends on the maximum temperature the target can reach over an extended time, which could be on the order of hours. Although the temperatures used for treatment generally do not exceed 42 C, some treatments near 50 C have been performed. Such higher temperatures are of interest since increasing the temperature allows exposure time to be reduced. For example, a hyperthermia treatment can be performed by increasing the local body temperature to about 50 C. However, such therapies are still reported to require exposure times on the order of 0.1 hours (6 minutes). [See, e.g., Dickson, J. A. and Calderwood, S. K., 1980, "Temperature Range and Selective Sensitivity of Tumors to Hyperthermia: A Critical Review," Annals New York Academy of Sciences, Vol. 335, pp. 180-205].

In treating tumors or other cancers, it is desirable that the tumor be locally heated such that healthy tissue remains unaffected. Such a treatment can be affected through external approaches, such as that undertaken for treating skin cancer. An external approach to treating skin cancer, for example, utilizes high frequency microwaves with slight tissue penetration depth to induce cell death in melanoma tumors. For treating deeper lying tumors, however, existing methods generally rely on the insertion of heat sources directly into a tumor to induce cell death or to cause ablation. To overcome the drawbacks associated with such an approach, there has been a move in the field to focus electromagnetic radiation in deeper lying tissues to reach the tumor. Care must be taken, however, to limit the diffusion of heat throughout healthy tissue that surrounds the tumor.

SUMMARY

Embodiments of the present invention describe systems and methods for treating patients with electromagnetic radiation to cause rapid heating of tissue and to thereby induce cell death. In a first embodiment of the invention, a method of treating a patient is provided. The method includes identifying a target that contains biological tissue and directing electromagnetic radiation at the target, where the electromagnetic radiation causes a temperature increase per unit of time in the biological tissue. In the method, the temperature increase per unit of time causes the change in the cell function in the biological tissue and is within a range of approximately one degree Celsius per second to approximately one degree Celsius per microsecond.

In a second embodiment of the invention, a method for treating a patient is provided. The method includes positioning a target to receive electromagnetic radiation. The method also includes changing a cell function in the target by directing electromagnetic radiation towards the target such that a temperature increase per unit of time associated with the electromagnetic radiation causes heating in the target and the temperature increase per unit of time is within a range of approximately one degree Celsius per second to approximately one degree Celsius per microsecond.

In a third embodiment of the invention, a system for treating a patient is provided. The system includes an antenna that emits electromagnetic radiation and a reflector that receives the electromagnetic radiation from the antenna, where the reflector is configured to direct at least a portion of the electromagnetic radiation from the antenna to a target to change a cell function in biological tissue of the target. In the system, the electromagnetic radiation directed at the target causes a temperature increase per unit of time in the biological tissue and the temperature increase per unit of time causes the change in the cell function in the biological tissue and is within a range of approximately one degree Celsius per second to approximately one degree Celsius per microsecond.

BRIEF DESCRIPTION OF THE DRAWINGS

Embodiments of the present application will now be described, by way of example only, with reference to the attached Figures, wherein.

DETAILED DESCRIPTION

Figure 1:
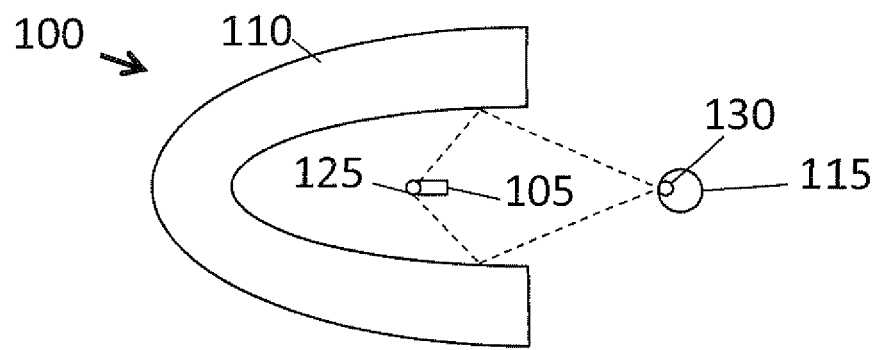
FIG. 1 illustrates an example of a system for treating a patient in accordance with an embodiment of the invention.

The present invention is described with reference to the attached figures, wherein like reference numerals are used throughout the figures to designate similar or equivalent elements. The figures are not drawn to scale and they are provided merely to illustrate the instant invention. Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. In other instances, well-known structures or operations are not shown in detail to avoid obscuring the invention. The present invention is not limited by the illustrated ordering of acts or events, as some acts may occur in different orders and/or concurrently with other acts or events. Furthermore, not all illustrated acts or events are required to implement a methodology in accordance with the present invention.

Several definitions that apply throughout this document will now be presented. The word "patient" is defined as any living organism that is capable of receiving treatment for an ailment or some other medical or cosmetic condition. A "target" is defined as tissue towards which electromagnetic radiation may be intentionally directed to cause some change in the tissue. "Biological tissue" means any living tissue. The term "electromagnetic radiation" means radiation consisting of electromagnetic waves. A "cell function" is defined as a biological activity, process, behavior or result that a cell is capable of performing, exhibiting or undergoing. The term "cell death" is defined as the biological death of a cell.

An "antenna" is defined as a structure that is capable of at least emitting electromagnetic radiation. A "reflector" is defined as a structure that receives electromagnetic radiation from an antenna and reflects the electromagnetic radiation substantially towards a target. The term "focal point" means a point at which radiation converges or from which radiation diverges. A "lens" is defined as a medium that is configured to alter the convergence or divergence of electromagnetic radiation. The term "coupling medium" is defined as a medium, other than atmospheric air, that engages a surface and through which electromagnetic radiation may pass.

As noted earlier, the process of heating tissue to temperatures that will induce cell death has been used as a form of cancer treatment. However, as also has been noted, such treatments generally require extended exposure of the tissue to electromagnetic radiation, which can take minutes or even hours. Generally, the result of such treatments is generation of heat at the target and dissipation of heat from the target to the surrounding normal tissues. Accordingly, throughout the treatment, the heat accumulation at the target also has to overcome heat losses to surrounding normal tissues so the target can maintain the therapeutic temperature. Unfortunately, such heat losses to the surrounding normal tissues within the extended treatment time increase the heat loading to the patient. Therefore, it is desirable to reduce the exposure time in order to reduce such heating effects in the normal tissues, yet still maintain therapeutic effectiveness at the target for patient treatments.

In view of these issues and the limitations of conventional hyperthermic therapies, the various embodiments of the invention provide a system and method for treating target tissues in a patient using a hyperthermic treatment that minimizes the impact on surrounding tissues. In the various embodiments of the invention, such treatments are achieved through exposure of a target biological tissue to high power electromagnetic energy, such as microwave energy, but with a duration of approximately one (1) second or less. Through such treatments, a rapid temperature rise per unit of time (up to 1 degree/microsecond) can be achieved to reduce exposure times. Further, while the resulting maximum temperature may be above or below the typical therapeutic temperature for hyperthermia (e.g., 42 C), the present inventors have discovered that it is the temperature rise per unit of time at the target that causes significant the change of cell function (e.g., cell death).

In the various embodiments of the invention, methods are provided for that can include the steps of identifying a target that contains biological tissue and directing electromagnetic radiation at the target to change a cell function in the biological tissue. The electromagnetic radiation can cause a temperature increase per unit of time in the biological tissue. In addition, the temperature increase per unit of time can be within a range of approximately one degree Celsius per second to approximately one degree Celsius per microsecond and can cause the change in the cell function, including cell death, in the biological tissue. This process can induce cell death in the target but can limit the patient's thermal exposure and total energy deposition in the patient's body, particularly in comparison to prior art techniques.

FIG. 1 illustrates an example of a system for treating a patient in accordance with an embodiment of the invention. The system 100 can include an antenna 105 that is capable of emitting one or more pulses of electromagnetic radiation. The system 100 can also include a reflector 110 that can receive the pulses of electromagnetic radiation from the antenna 105. The reflector 110 can also be configured to direct at least a portion of the pulses of electromagnetic radiation from the antenna 105 to a target 115. As an example, the reflector 110 can be a prolate-spheroidal reflector, as shown in FIG. 1, although other configurations can be employed in the various embodiment of the invention. The target 115 can contain biological tissue and can be in or on the patient (not shown). As will be explained in detail below, this direction of electromagnetic radiation to the target 115 can change a cell function in the biological tissue of the target 115.

In the configuration illustrated in FIG. 1, the antenna 105 can emit the pulse of electromagnetic radiation towards the reflector from a first focal point 125 of the reflector 110, and the target 115 can be substantially aligned with a second focal point 130 of the reflector 110. That is, the portion of target 115 that is to receive the electromagnetic radiation can be substantially aligned with the second focal point 130 of reflector 110. The dashed lines in FIG. 1 are illustrative of the path that a portion of the electromagnetic radiation emitted at first focal point 125 may take to arrive at the second focal point 130 and, correspondingly, at the portion of target 115 aligned with second focal point 130.

Figure 2:
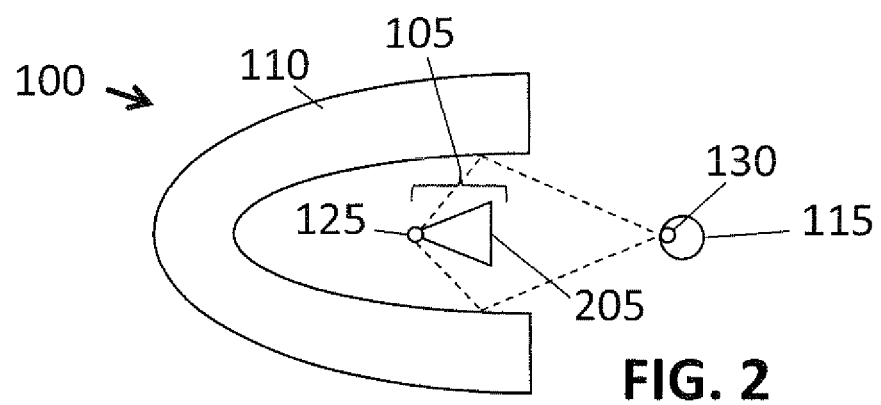
FIG. 2 illustrates an exemplary alternate configuration, in accordance with the various embodiments of the invention, for the system of FIG. 1.
Figure 3:
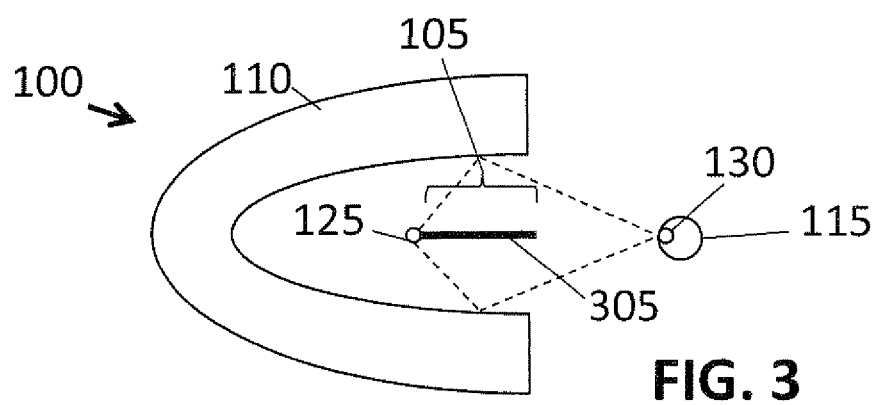
FIG. 3 illustrates another exemplary alternate configuration, in accordance with the various embodiments of the invention, for the system of FIG. 1.

The antenna 105 can be in the form of any structure that is capable of emitting one or more pulses of a desired type of electromagnetic radiation. For example, FIGS. 2 and 3 illustrate exemplary alternate configurations, in accordance with the various embodiments of the invention, for the system 100 of FIG. 1. As shown in FIG. 2, the antenna 105 of the system 100 can be a conical antenna 205 configured to emit radiation at focal point 125 of reflector 110. Alternatively, as shown in FIG. 3, the antenna 105 of the system 100 can be a monopole antenna 305 configured to emit radiation at focal point 125. However, the various embodiments of the invention are not limited in this regard. Therefore, any other types of other feed and/or antenna structures may be used in the various embodiments of the invention.

Figure 4:
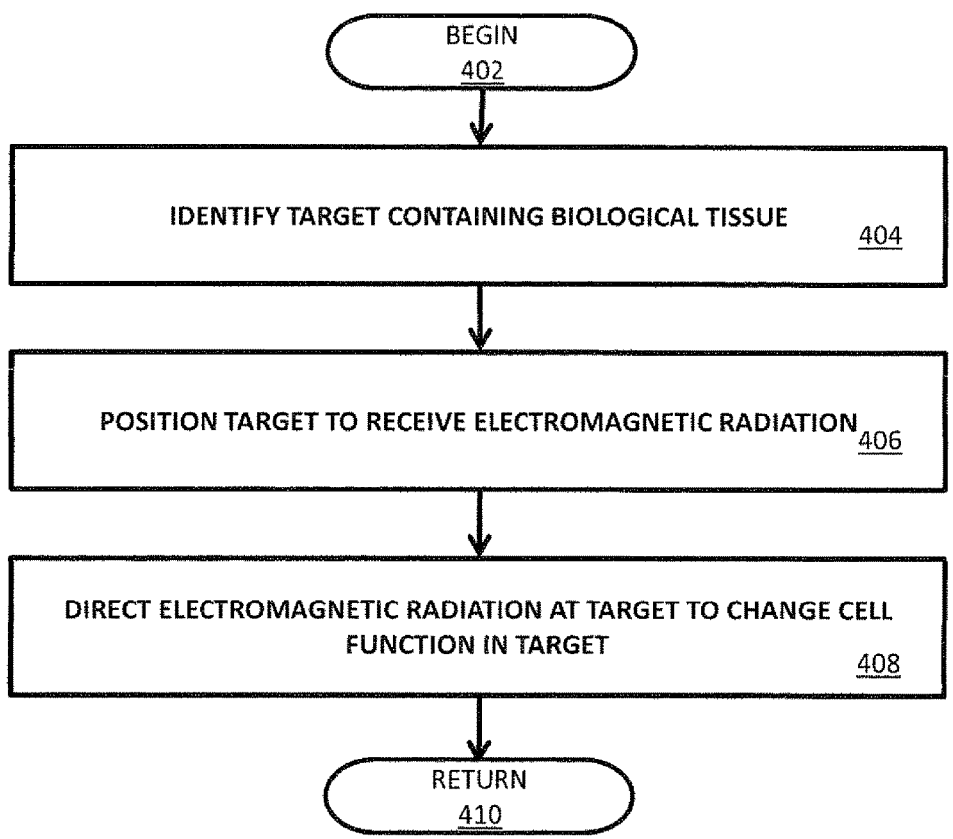
FIG. 4 is a flowchart of step in an exemplary method for treating a patient in accordance with an embodiment of the invention.

Referring now to FIG. 4, a method 400 for treating a patient is shown. To describe the method 400, reference will be made to FIG. 1 for illustrative purposes. However, the method 400 can also be performed using any other system in accordance with an embodiment of the invention. Moreover, the method 400 is not necessarily limited to the order depicted in FIG. 4, as the steps may be executed in a different chronology. Further, the method 400 may also contain additional steps beyond what is shown here or even a fewer number of steps.

Method 400 begins at step 402 and continues to step 404. At step 404, a target that contains biological tissue can be identified. Such identification can be performed using any type of method, including surgical and imaging methods. Afterwards, at step 406, the target can be positioned to receive electromagnetic radiation. For example, a patient may be afflicted with a condition in which the patient's body contains unwanted biological tissue. The biological tissue may contain, for example, cancerous tissue or adipose tissue. Referring to FIG. 1, this biological tissue can be identified in target 115, and the target 115 can be positioned in an appropriate location with respect to the system 100. That is, the unwanted biological tissues can be substantially aligned with second focal point 130.

Thereafter, at step 408, at least one pulse of electromagnetic radiation can be directed at the target to change a cell function in the biological tissue of the target. For example, as described above with respect to FIG. 1, the antenna 105 can emit one or more pulses of electromagnetic radiation towards the reflector 110. The reflector 110 can then direct at least a portion of the electromagnetic radiation to the target 115. For example, the emission of the electromagnetic radiation can occur at the first focal point 125 and can be substantially directed to the target 115 at the second focal point 130, as described above. Once the electromagnetic radiation is directed to the target at step 408, the method can continue to step 410 to end or perform additional steps or processes, including repeating method 400.

The pulses of electromagnetic radiation directed to the target can cause a temperature increase per unit of time in the biological tissue of the target 115. This temperature increase per unit of time causes heating in the target 115, and the temperature increase per unit of time can be in a range from approximately one degree Celsius per second to approximately one degree Celsius per microsecond. This range represents values that are much higher than those used for conventional treatments, in which heat treatments rely on sustaining an effective temperature, and it has been shown that a temperature increase per unit of time in this range causes a change in cell function of the tissue in the target 115. For example, the present inventors have found that cell death in the target 115 can been induced in response to this range, which can be useful in the treatment of cancerous tumors. In addition, for an increase in the temperature increase per unit of time associated with the electromagnetic radiation, there is a corresponding increase in the cell death rate of the target 115. In the various embodiments of the invention, the temperature increase per unit of time can be adjusted by varying the power density (power per unit area) of the electromagnetic radiation at the position of the biological tissue. Such an adjustment is illustrated in FIG. 5.

Figure 5:
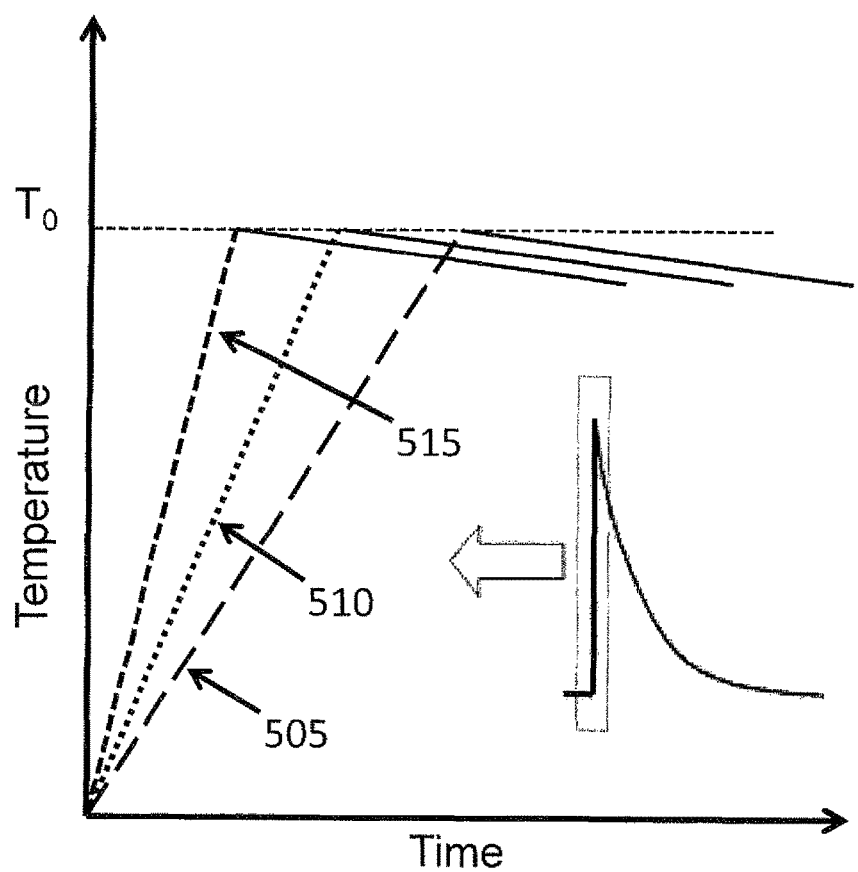
FIG. 5 is an schematic graph showing the temporal development of temperature in a sample exposed to electromagnetic radiation for various rates of temperature rise.

FIG. 5 is an X-Y plot showing schematically the temporal development of temperature in a target tissue exposed to a pulse of electromagnetic radiation for different rise times or rates. In particular, FIG. 5 shows the portion of the pulse associated with an increase in temperature, as indicated in the inset in FIG. 5. The inset in FIG. 5 shows the entire temporal development, rise and fall of the temperature, but on a longer time scale.

In FIG. 5, curve 505 represents a lower rate, curve 510 represents a higher rate, and curves 515 an even higher rate of temperature increase. In the various embodiments of the invention, such rise times or rates can be adjusted by changing a power density of the electromagnetic radiation. That is, the higher the power density, the faster is the rise in temperature, and vice versa. The total temperature increase or maximum temperature ($T_0$) is kept constant for this example. This can be achieved by reducing the time of electromagnetic radiation exposure for higher power levels and increasing the time of exposure for lower power levels, respectively. After exposure, and after reaching $T_0$, the tissue temperature decays due to losses through thermal diffusion to neighboring, colder tissue. This can be a process which takes much longer than the exposure time of the tissue to electromagnetic radiation, as shown in the inset in FIG. 5. Generally, regardless of the rise time, the decay rate and time will be substantially similar. However, as described above, the rise time or rate will most strongly affect biological effects on the target tissues. This is shown in FIG. 6.

Figure 6:
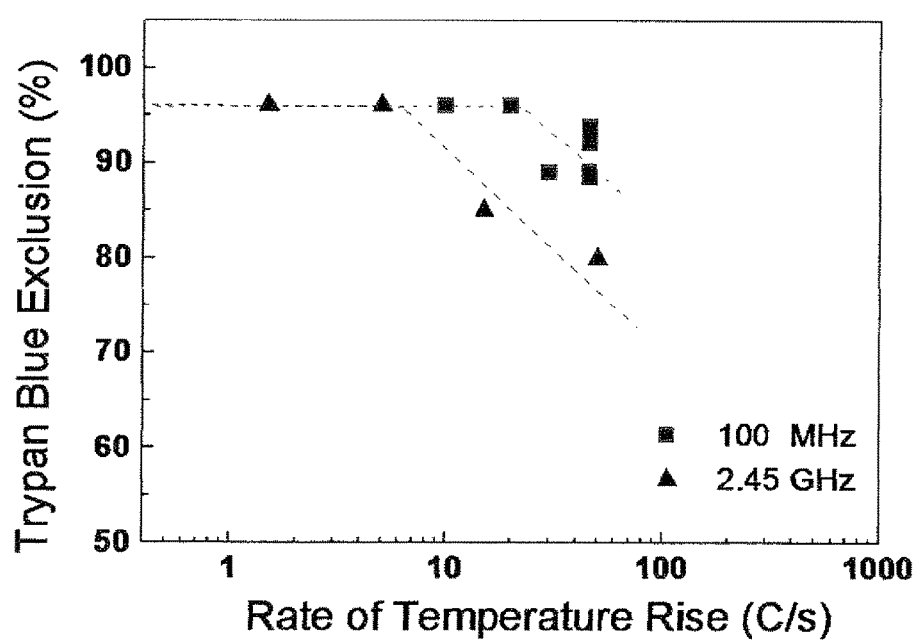
FIG. 6 is a semi-log plot of measured trypan blue exclusion versus rate of temperature rise for cells exposed to narrowband microwave radiation for various amounts of overall temperature increase.

FIG. 6 is a semi-log plot of cell viability (using trypan blue uptake as an assay) versus rate of temperature rise for murine liver cancer cells exposed to narrowband microwave radiation at 100 MHz and 2.45 GHz for various rates of temperature increase. The maximum temperature ($T_0$) was held to 45 C in this experiment. As known to one or ordinary skill in the art, trypan blue uptake or exclusion, respectively, can be used to monitor and evaluate the degree of cell death or cell viability, respectively. Reduced trypan blue exclusion corresponds to increased degree of cell death. Plotted are average values of the trypan blue exclusion versus temperature rate of rise.

FIG. 6 shows that when the cancer cells were exposed to 100 MHz radiation (indicated by squares in FIG. 6), the cell viability was generally unaffected by temperature rates of rise below approximately 10 C/s, and then decreases to approximately 90% for temperature rates of rise of approximately 50 C/s. In other words, cell death rate rises above a threshold in temperature rate of rise.

However, biological effects can also be adjusted via the type (i.e., frequency) of electromagnetic radiation. For example, as shown in FIG. 6, an increase from 100 MHz to 2.45 GHz, results in a further increase of cell death. This is shown in the results using 2.45 GHz radiation (triangles) to increase the temperature by 20 C beginning at room temperature (22.5 C) with various temperature rates of rise. Plotted are average values of the trypan blue exclusion versus temperature rate of rise. As shown in FIG. 6, the viability of liver cancer cells in suspension was found to decrease above temperature rate of rise values of approximately 10 C/s for 2.45 GHz radiation. At 50 C/s, the viability decreases to approximately 80%, as compared to 90% for 100 MHz radiation. Extrapolating this curve to 100% lethality would indicate that zero viability would occur for a temperature rate of rise of approximately 1000 C/s. This result is generally unexpected, since for a 20 K increase to 42.5 C and an exposure time of less than one (1) second, cell death through a hyperthermic treatment is not generally expected. [See, e.g., Wust, P. Hildebrandt, B., Sreenivasa, G., Rau, B., Gellermann, J., Riess, H., Felix, R., and Schlag, P. M., 2002, "Hyperthermia in combined treatment of cancer," The Lancet Oncology, 3, pp. 487-497. ] Rather, cell death through hyperthermia at this temperature would be expected to require an exposure time of approximately 20 hours [Dickson, J. A. and Calderwood, S. K., 1980, "Temperature Range and Selective Sensitivity of Tumors to Hyperthermia: A Critical Review," Annals New York Academy of Sciences, Vol. 335, pp. 180-205]. Thus, the increased fraction cell death is not a hyperthermia effect as the exposure times described herein are less than a second and is the result of another effect due primarily to the rate of temperature increase.

Therefore, in view of FIGS. 5, and 6, the electromagnetic radiation can be directed at the target 115 such that the target 115 is exposed to the electromagnetic radiation for a predetermined time period, using a relatively high rate of temperature increase so as to provide reduced energy deposition but sufficient therapeutic effects. As an example, the predetermined time period can be within a range of approximately one microsecond to approximately ten seconds. In comparison to previous techniques, the pulse duration for this treatment is much lower, which can dramatically decrease the thermal exposure time for patients. For example, some conventional hyperthermia treatments rely on pulse durations that are over six minutes long or even longer. In view of the temperature increase per unit of time being higher as described herein, the patient's overall thermal exposure is reduced. Moreover, the overall energy deposition in the patient is reduced in comparison to prior hyperthermia treatments. As such, the healthy tissue surrounding the target 115 is affected to a lesser extent as compared to conventional methods.

Although various exposure times or pulse durations, temperature rise rates, and total temperature amounts are specified above, the various embodiments of the invention are not limited to any specific combination of these values. Rather, in the various embodiments of the invention any combination of pulse duration, temperature rise rate and total temperature rise can be used to accommodate the type of treatment. For example, it is possible to increase temperatures by as much as 100 degrees for short exposure times.

In the various embodiments of the invention, the electromagnetic radiation has a frequency within a range of approximately one hundred megahertz (MHz) to approximately one hundred gigahertz (GHz). Since the depth of penetration decreases with increasing frequency. The frequency of the electromagnetic radiation can therefore be adjusted to accommodate certain conditions, if desired. For example, the frequency of the electromagnetic radiation can be determined based on the depth of penetration necessary to reach the target 115. Such a condition may be the case when a target 115 is embedded under the skin of a patient. The frequency of the electromagnetic radiation, however, is not necessarily limited to this particular range, as other suitable values may be applicable.

Further, a range of power densities can be used in the various embodiments of the invention. For example, power densities can be in the range of 100 W/kg (corresponding to conventional dosages for hyperthermia) to 100 MW/Kg (corresponding to a 10 C/ns temperature rise rate).

Referring back to method 400, electromagnetic radiation is described as being directed to a target at step 408 by reflecting the radiation to a target 115 using reflector 110. In particular, by arranging the target 115 to coincide with the second focal point 130. However, in some cases, if there are imperfections in the radiation pattern of the antenna 105, the reflector 105, and or alignment of target 115 with second focal point 130, the electromagnetic radiation may not correctly reach the target. Therefore, in some embodiments of the invention, additional components can be included with system 100 to improve directing of radiation to target 115.

Figure 7:
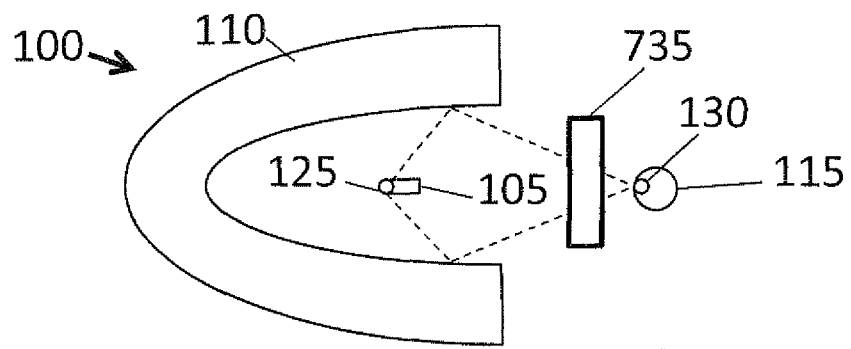
FIG. 7 illustrates the system of FIG. 1 including an exemplary lens structure.

For example, in some embodiments of the invention, a lens or other focusing feature can be used to correct such alignment issues. Further, such a lens or focusing feature can also be used generally to improve resolution and provide higher intensity at the second focal point 130. This is illustrated in FIG. 7. FIG. 7 illustrates the system of FIG. 1 including an exemplary lens structure. As shown in FIG. 7, in addition to the various components described above with respect to system 100 in FIG. 1, at least one lens 735 can be included. For example, in some embodiments of the invention, lens 735 can comprise an electromagnetic lens to generate one or more electric fields to redirect and focus electromagnetic radiation from reflector to a point on the target. Such a lens can also be used generally to improve resolution and provide higher intensity at the second focal point 130. Such lenses are well-known to those of ordinary skill in the art and will not be described here. However, the various embodiments of the invention are not limited to electromagnetic lenses. In other embodiments of the invention, an adjustable reflector can be used, which can be mechanically deformed and/or repositioned to focus electromagnetic radiation from reflector at a point on the target. In yet other embodiments any combination of lenses and reflectors can be used.

Figure 8:
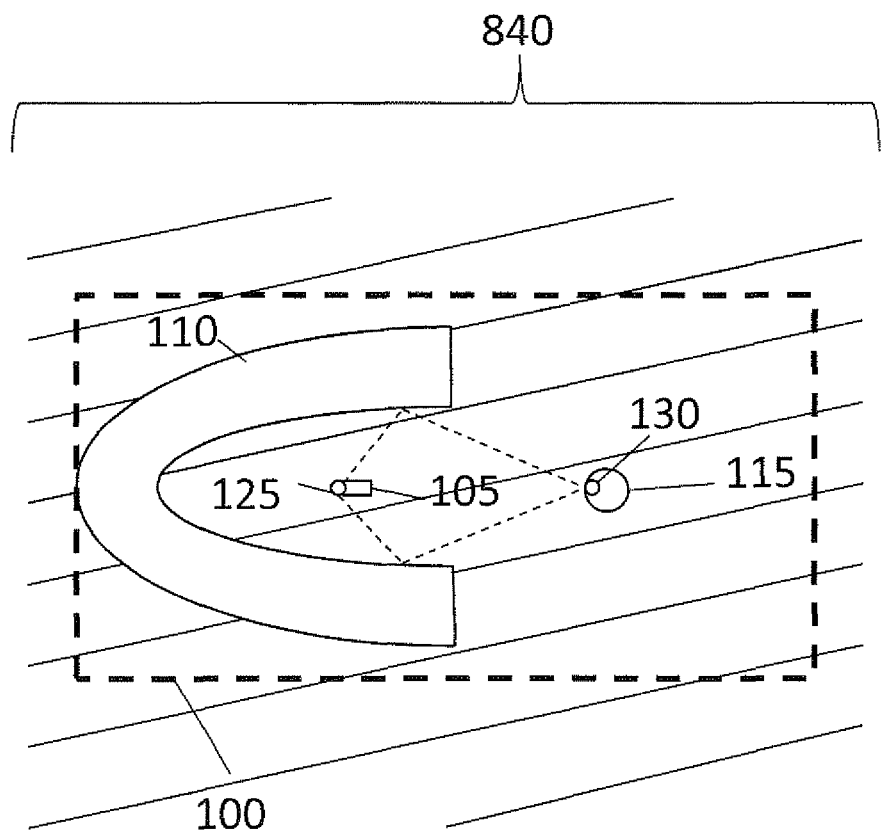
FIG. 8 illustrates the system of FIG. 1 in an exemplary coupling medium.

In some embodiments of the invention, alternatively or in addition to lenses, a coupling medium can be used to direct electromagnetic energy to a point on a target. For example, FIG. 8 illustrates the system of FIG. 1 using an exemplary coupling medium. As shown in FIG. 8, system 100 can be adapted so that the target 115 is positioned in a coupling medium. 840. In particular, coupling medium 840 can be configured to comprise a material having similar properties as the target tissues. Thus, a lower amount of radiation is reflected by the interface defined by a surface of tissue 115. As a result, more of the radiation received from the reflector can be directed to the target 115. For example, the target can be submerged in water or any other fluid with dielectric properties similar to tissue 115 and that allows a more efficient coupling of the electromagnetic radiation from antenna 105 to target 115. However, the various embodiments of the invention are not limited in this regard and other coupling mediums can be used.

Applicants present certain theoretical aspects above that are believed to be accurate that appear to explain observations made regarding embodiments of the invention. However, embodiments of the invention may be practiced without the theoretical aspects presented. Moreover, the theoretical aspects are presented with the understanding that Applicants do not seek to be bound by the theory presented.

While various embodiments of the present invention have been described above, it should be understood that they have been presented by way of example only, and not limitation. Numerous changes to the disclosed embodiments can be made in accordance with the disclosure herein without departing from the spirit or scope of the invention. Thus, the breadth and scope of the present invention should not be limited by any of the above described embodiments. Rather, the scope of the invention should be defined in accordance with the following claims and their equivalents.

Although the invention has been illustrated and described with respect to one or more implementations, equivalent alterations and modifications will occur to others skilled in the art upon the reading and understanding of this specification and the annexed drawings. In addition, while a particular feature of the invention may have been disclosed with respect to only one of several implementations, such feature may be combined with one or more other features of the other implementations as may be desired and advantageous for any given or particular application.

The terminology used herein is for the purpose of describing particular embodiments only and is not intended to be limiting of the invention. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising." Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

What is claimed is:

1. A system for treating a patient, comprising:
   a pulse source configured for generating one or more pulses of electromagnetic radiation;
   an antenna coupled to the pulse source and configured to emit the one or more pulses of the electromagnetic radiation; and
   a reflector that receives the one or more pulses of electromagnetic radiation from the antenna,
   wherein the reflector is configured to direct at least a portion of the electromagnetic radiation in the one or more pulses of the electromagnetic radiation from the antenna to a target within biological tissue, wherein the portion of the electromagnetic radiation directed at the target causes a temperature increase per unit of time in the biological tissue greater than one degree Celsius per second and less than or equal to approximately one degree Celsius per microsecond, and wherein the temperature increase per unit of time causes cell death in the biological tissue regardless of a maximum temperature being above or below a therapeutic temperature for hyperthermia.

2. The system according to claim 1, wherein the antenna emits the one or more pulses of the electromagnetic radiation towards the reflector at a first focal point of the reflector and the target is substantially aligned with a second focal point of the reflector.

3. The system according to claim 1, wherein the reflector is a prolate-spheroidal reflector.

4. The system according to claim 1, further comprising a lens that is positioned between the reflector and the target, and wherein the lens is configured to increase the intensity of the portion of the electromagnetic radiation directed to the target.

5. The system according to claim 1, wherein at least a portion of the system operates in a coupling medium.

6. The system according to claim 1, wherein the pulse source is configured for generating the one or more pulses of the electromagnetic radiation so that the electromagnetic radiation has a frequency that is within the range of approximately one hundred megahertz to approximately one hundred gigahertz.

7. The system according to claim 1, wherein the temperature increase is greater than or equal to 10 degrees Celsius per second.

8. The system according to claim 1, wherein the temperature increase is less than or equal to 1000 degrees Celsius per second.

9. The system according to claim 6, wherein the frequency is determined based on at least a depth of penetration to reach the target.

10. The system according to claim 1, wherein a power density level of the electromagnetic radiation at the target is within a range of approximately one hundred watts per kilogram to one hundred megawatts per kilogram.

11. The system according to claim 1, wherein the biological tissue comprises a cancer tissue or adipose tissue.

12. The system according to claim 1, wherein the system is configured to allow varying a power density of the electromagnetic radiation at a position of the biological tissue to adjust the temperature increase per unit of time.

13. The system according to claim 1, wherein the reflector is an adjustable reflector configured to be mechanically deformed or mechanically repositioned to focus electromagnetic radiation.

14. The system according to claim 1, wherein the system is configured to keep a total temperature increase at a selected constant.

* * * * *